United States Patent
Murata et al.

(10) Patent No.: US 7,375,103 B2
(45) Date of Patent: *May 20, 2008

(54) OPTICALLY ACTIVE PYRIDINE DERIVATIVE AND A MEDICAMENT CONTAINING THE SAME

(75) Inventors: Toshiki Murata, Nara-ken (JP); Sachiko Sakakibara, Aichi-ken (JP); Takashi Yoshino, Nara-ken (JP); Hiroki Sato, Nara-ken (JP); Yuji Koriyama, Nara-ken (JP); Noriko Nunami, Nara-ken (JP); Megumi Yamauchi, Nara-ken (JP); Keiko Fukushima, Nara-ken (JP); Rolf Grosser, Leverkusen (DE); Kinji Fuchikami, Kyoto-fu (JP); Kevin Bacon, Hyogo (JP); Timothy Lowinger, Guilford, CT (US)

(73) Assignee: Bayer HealthCare AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/508,107

(22) PCT Filed: Mar. 3, 2003

(86) PCT No.: PCT/EP03/02169

§ 371 (c)(1),
(2), (4) Date: May 16, 2005

(87) PCT Pub. No.: WO03/076447

PCT Pub. Date: Sep. 18, 2003

(65) Prior Publication Data

US 2005/0215547 A1    Sep. 29, 2005

(30) Foreign Application Priority Data

Mar. 14, 2002  (JP)  ............... 2002-070655

(51) Int. Cl.
*C07D 498/04* (2006.01)
*A61K 31/5365* (2006.01)
*A61P 29/00* (2006.01)

(52) U.S. Cl. .................... 514/230.5; 544/91

(58) Field of Classification Search ............ 544/91; 514/230.5
See application file for complete search history.

(56) References Cited

FOREIGN PATENT DOCUMENTS

WO          0224679          3/2002

OTHER PUBLICATIONS

Manna, F., et al., "Anti-inflammatory, analgesic and antipyretic 4,6-disubstituted 3-cyano-2-aminopyridines", Eur. J. Med. Chem., 34(3): 245-254 (Mar. 1999).

*Primary Examiner*—Kahsay T Habte
(74) *Attorney, Agent, or Firm*—Edwards Angell Palmer & Dodge, LLP; Ralph A. Loren

(57) ABSTRACT

An optically active (−)-7-[2-(cyclopropylmethoxy)-6-hydroxyphenyl]-5-[(3S)-3-piperidinyl]-1,4-dihydro-2H-pyrido[2,3-d][1,3]oxazin-2-one of the formula (I) or salt thereof. The compound has an excellent anti-inflammatory activity, and other biological activity (I)

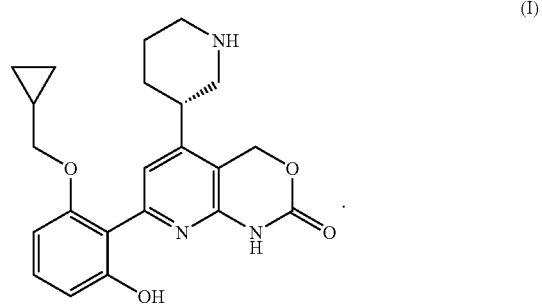

6 Claims, No Drawings

OPTICALLY ACTIVE PYRIDINE DERIVATIVE AND A MEDICAMENT CONTAINING THE SAME

DETAILED DESCRIPTION OF INVENTION

1. Technical Field

The present invention relates to (−)-7-[2-cyclopropylmethoxy)-6-hydroxyphenyl]-5-[(3S)-3-piperidinyl]-1,4-dihydro-2H-pyrido[2,3-d][1,3]oxazin-2-one, a salt thereof, pharmaceutical preparations containing them. (−)-7-[2-(Cyclopropylmethoxy)-6-hydroxyphenyl]-5-[(3S)-3-piperidinyl]-1,4-dihydro-2H-pyrido[2,3-d][1,3]oxazin-2-one of the present invention inhibits IκB kinase β (IKK-β or IKK-beta) activity, thus inhibit nuclear factor kappa B (NF-κB) activity, and can be used for the prophylaxis and treatment of diseases associated with NF-κB activity, in particular for the treatment of inflammatory diseases.

2. Background Art

Nuclear factor kappa B (NF-κB) belongs to a family of closely related homo- and hetero-dimeric transcription factor complexes composed of various combinations of the Rel/NF-κB family of polypeptides. NF-κB and related family members are involved in the regulation of more than 50 genes relating to immune and inflammatory responses ((Barnes P J, Karin M (1997) N Engl J Med 336, 1066-1071) and (Baeuerle P A, Baichwal V R (1997) Adv Immunol 65, 111-137)). In most cell types, NF-κB is present as a heterodimer comprising a 50 kDa and a 65 kDa subunit (p50/RelA). The heterodimer is sequestered in the cytoplasm in association with inhibitor of NF-κB (IκB)-family of proteins to be kept in an inactive state. IκB-family proteins mask the nuclear translocation signal of NF-κB. Upon stimulation of cells with various cytokines (e.g. TNF-α, IL-1), CD40 ligand, lipopolysaccharide (LPS), oxidants, mitogens (e.g. phorbol ester), viruses or many others. IκB proteins are phosphorylated at specific serine residues, polyubiquitinated, and then degraded through a proteasome-dependent pathway. Freed from IκB, the active NF-κB is able to translocate to the nucleus where it binds in a selective manner to preferred gene-specific enhancer sequences. Among the genes being regulated by NF-κB are many coding for pro-inflammatory mediators, cytokines, cell adhesion molecules, and acute phase proteins. Expression of several of these cytokines and mediators in turn can lead to further activation of NF-κB via autocrine and paracrine mechanisms.

Broad evidence is available that suggests a central role of NF-κB in many inflammatory disorders including airway inflammation and asthma ((Yang L et al., J Exp Med 188 (1998), 1739-1750), (Hart L A et al. Am J Respir Crit Care Med 158 (1998), 1585-1592), (Stacey M A et al., Biochem Biophys Res Commun 236 (1997), 522-526) (Barnes P and Adcock I M, Trends Pharmacol Sci 18 (1997), 46-50)).

Further, it has been shown that glucocorticoids, which are by far the most effective treatment for asthma, inhibit airway inflammation by directly interacting with and inhibiting the activity of the transcription factors NF-κB and activating peptide-1 (AP-1) ((Barnes P (1997) Pulmon Pharmacol Therapeut 10, 3-19) and (Dumont A et al. (1998) Trends Biochem Sci 23, 233-235)).

In general, inhibition of NF-κB activation results in strong anti-inflammatory effects similar or superior to those brought upon by steroids. Consequently, NF-κB inhibition should improve inflammatory symptoms typical for asthma; allergic rhinitis; atopic dermatitis; hives; conjunctivitis; vernal catarrh; rheumatoid arthritis; systemic lupus erythematosus; psoriasis; diabrotic colitis; systemic inflammatory response syndrome; sepsis; polymyositis; dermatomyositis; Polyaritis nodoa; mixed connective tissue disease; Sjoegren's syndrome; gout, and the like.

Further, several studies imply that NF-κB plays an essential role in neoplastic transformation. For example, NF-κB is associated with cell transformation in vitro and in vivo as a result of gene overexpression, amplification, rearrangement, or translocation (Mercurio, F., and Manning, A. M. (1999) Oncogene, 18: 6163-6171). In certain human lymphoid tumor cells, the genes of NF-κB family members are rearranged or amplified. Its possible involvement in cancer pathology is also disclosed in Mayo, M. W., Baldwin A. S. (2000) Biochmica et Biophysica Acta 1470 M55-M62. Mayo M. W. et al., discloses the inhibition of NF-κB results in the blockage the initiation and/or progression of certain cancer, particularly colorectal cancer.

Finally, NF-κB may also be involved in the regulation of neuronal cell death. It has been shown that NF-κB becomes activated and promotes cell death in focal cerebral ischemia (Nature medicine Vol. 5 No. 5, May 1999).

Extensive research during the past years led to the identification of an IκB kinase (IKK) complex as being responsible for the signal-induced IκB phosphorylation ((Mercurio, F., and Manning, A. M. (1999) Current Opinion in Cell Biology, 11: 226-232), (Mercurio, F., and Manning, A. M. (1999) Oncogene, 18: 6163-6171), (Barnkett, M., and Gilmore T. D. (1999) Oncogene 18, 6910-6924), (Zandi, E., and Karin, M., (1999) 19: 4547-4551), (Israel, A., (2000) trends in CELL BIOLOGY. 10: 129-133), and (Hatada, E. N, et al. (2000) Current Opinion in Immunology, 12: 52-58)). This complex is most likely the site of integration of all of the different stimuli leading to NF-κB activation. The IKK-complex (molecular weight 700-900 kDa) is composed of various proteins including two homologous IκB kinases, called IKK-α and IKK-β, an upstream kinase, NIK which induces NF-κB, a scaffold protein called IKAP, which tethers together the three kinases, and a regulatory subunit IKK-γ, which preferentially interacts with IKK-β.

IKK-β is a 756 amino acid serine-threonine kinase showing 52% identity to and the same domain structure as IKK-α ((Mercurio F et al. (1997) Science 278, 860-866.), (Woronicz J D et al. (1997) Science 278, 866-869.), (Zandi E et al. (1997) Cell 91, 243-252.). IKK-β forms homo-dimers and hetero-dimers with IKK-α in vitro and in cells, respectively. IKK-β also interacts with IKK-γ, IKAP, NIK and IκBα. Recombinant IKK-β phosphorylates IκBα and IκBβ at specific serine residues with equal efficacy (Li J et al. (1998) J Biol Chem 273, 30736-30741.), (Zandi E, Chen Y, Karin M (1998) Science 281, 1360-1363.). IKK-β shows a higher constitutive kinase activity as compared to IKK-α. This is in agreement with data suggesting that over-expression of IKK-β activates the transcription of a NF-κB-dependent reporter gene with a higher efficacy as compared to IKK-α. IKK-β has been shown to be activated in various cell lines or fresh human cells in response to various stimuli including TNF-α, IL-1β, IL-1β, LPS, anti-CD3/anti-CD28 co-stimulation, protein kinase C and calcineurin, B-cell receptor/CD40 ligand stimulation, and vanadate. IKK-β is activated in fibroblast-like synoviocytes (FLS) isolated from the synovium of patients suffering from rheumatoid arthritis or osteoarthritis (Zandi E et al. (1997) Cell 91, 243-252.), (O'Connell M A et al. (1998) J Biol Chem 273, 30410-30414.), (Kempiak S J et al. (1999) J Immunol 162, 3176-3187.). Furthermore, IKK-β can be activated by the structurally related upstream kinases MEKK-1 and NIK, most likely through phosphorylation of specific serine residues within the T-loop (activation loop) and by certain protein kinase C isoforms ((Nakano H et al. (1998) Proc Natl Acad Sci USA 95, 3537-3542.), (Lee F S et al. (1998) Proc Natl Acad Sci USA 95, 9319-9324.), (Nemoto S et al. (1998) Mol Cell Biol 18, 7336-7343.), (Lallena M J et al. (1999) Mol Cell Biol 19, 2180-2188.)). A catalytically inactive mutant of IKK-β has been shown to inhibit activation of NF-κB by TNF-α, IL-1β, LPS, anti-CD3/anti-CD28 stimulation ((Mercurio F et al. (1997) Science 278, 860-866.), (Woronicz J D et al. (1997) Science 278, 866-869.)). The same effects are observed when MEKK1 or NIK are overexpressed. Additionally, IKK-β mutations in the activation loop inhibited IL-1 and TNF-α signaling (Delhase M et al. (1999) Science 284, 309-313.). Based on the experimental results described above, there is clear-cut evidence for a pivotal involvement of IKK-β in various pathways leading to NF-κB activation.

In summary, the specific inhibition of IKK-β should result in a strong anti-inflammatory and immuno-modulatory effect in vivo with the potential of improving the underlying causes of asthma and other diseases. In addition, anti-tumor and anti-ischemic effects of an IKK-β inhibitor may be expected.

Manna et al., disclose 4,6-disubstituted 3-cyano-2-aminopyridines represented by general formula:

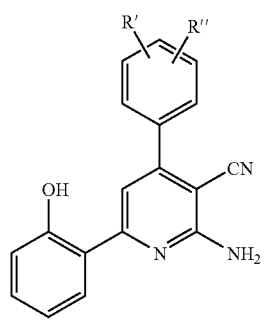

wherein
(R', R") represent (OCH₃, OCH₃), (Cl, Cl), (H, Cl), (H, Br), (H, CH₃), (H, OCH₃), (H, NO₂), or (H, N(CH₃)₂), or

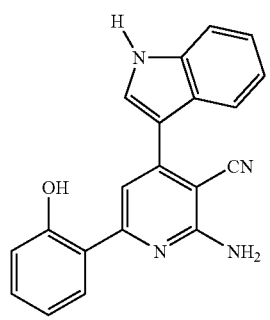

as a general anti-inflammatory, analgesic, and antipyretic agent (Eur J. Med. Chem. 34, 245-254(1999)).

Manna et al. neither disclose pyridine derivatives with aliphatic groups at position 4 of the pyridine ring, nor suggest IKK-β kinase or NF-κB inhibitory activity on the above known pyridine derivatives.

The development of a novel compound having effective anti-inflammatory actions based on a specific and selective inhibitory activity to IKK-β kinase has been desired.

SUMMARY OF THE INVENTION

As the result of extensive studies on chemical modification of pyridine derivatives, the present inventors have found that the compounds of novel chemical structure related to the present invention have unexpectedly excellent IKK-β kinase inhibitory activity. This invention is to provide (−)-7-[2-(cyclopropylmethoxy)-6-hydroxy-phenyl]-5-[(3S)-3-piperidinyl]-1,4-hydro-2H-pyrido [2,3-d][1,3]oxazin-2-one of the formula (I):

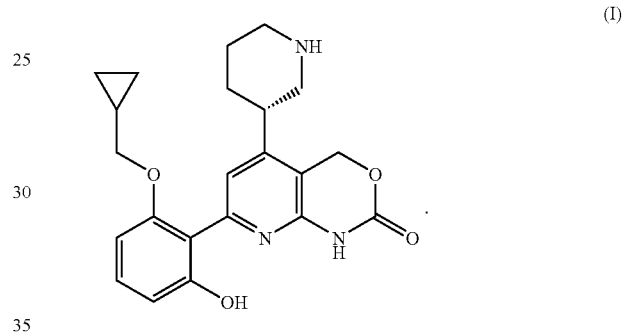

and the salts thereof:

The compound of the present invention is optically active and surprisingly shows excellent IKK-β kinase inhibitory activity, cytokine inhibitory activity, and anti-inflammatory activity in vivo even stronger than corresponding racemic modification or its enantiomer (+)-7-[2-(cyclopropylmethoxy)-6-hydroxyphenyl]-5-[(3R)-3-piperidinyl]-1,4-dihydro-2H-pyrido[2,3d][1,3]oxazin-2-one. It is, therefore, suitable especially as a reagent to inhibit activation of NF-κB and in particular for the production of medicament or medical composition, which may be useful to treat NF-κB dependent diseases.

More specifically, since (−)-7-[2-(cyclopropylmethoxy)-6-hydroxyphenyl]-5-[(3S)-3-piperidinyl]-1,4-dihydro-2H-pyrido [2,3-d][1,3]oxazin-2-one of the present invention inhibits IKK-β kinase activity, it is useful for treatment and prophylaxis of diseases involving NF-κB activity as follows: inflammatory symptoms including asthma; allergic rhinitis; atopic dermatitis, hives; conjunctivitis; vernal catarrh; chronic arthrorheumatism; systemic lupus erythematosus; psoriasis; diabrotic colitis; systemic inflammatory response syndrome (SIRS); sepsis; polymyositis; dermatomyositis (DM); Polyaritis nodoa (PN); mixed connective tissue disease (MCTD); Sjoegren's syndrome; gout; and the like.

The compound of the present invention is also useful for treatment and prophylaxis of diseases like ischemia and tumor, since the diseases also relate to IKK-β kinase and NF-κB activity.

The compound of the present invention can be prepared by combining various known methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (2$^{nd}$ Edition)" by Greene and Wuts.

The compound of the formula (II):

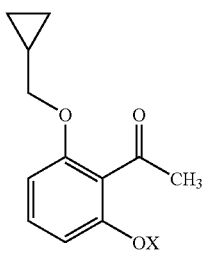

(II)

(wherein —OX represents hydroxyl group or protected hydroxy group by an appropriate protecting group (e.g., benzyl, methoxybenzy, and silyl)) is reacted with an aldehyde of the formula (III):

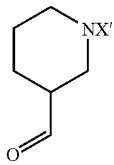

(III)

(wherein X' represents H or protecting group including, for instance, alkoxycarbonyl such as ethoxycarbonyl, tertiary butoxycarbonyl or the like: or other substituents which can be easily converted to H by conventional methods)

CNCH$_2$COOR$^1$     (IV)

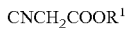

(wherein R$^1$ is CR$^{11}$R$^{12}$R$^{13}$, in which R$^{11}$, R$^{12}$ and R$^{13}$ are each independently C$_{1-6}$alkyl or aryl), and an ammonium salt such as ammonium acetate to obtain the compound represented by the formula (V):

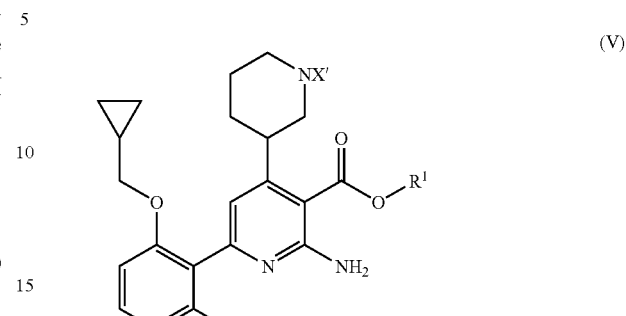

(V)

wherein
X, X', and R$^1$ are the same as defined above.

The reaction can be carried out without a solvent or in a solvent including, for instance, ethers, such as dioxane, and tetrahydrofuran; aromatic hydrocarbons such as benzene, toluene and xylene; nitriles such as acetonitrile; amides such as dimethyl-formamide (DMF) and dimethylacetamide; sulfoxides such as dimethyl sulfoxide, and others. The reaction temperature is usually, but not limited to, about 50° C. to 200° C. The reaction may be conducted for, usually, 30 minutes to 48 hours and preferably 1 to 24 hours. The compounds of the general formula (II), (III), (IV), and an ammonium salt such as ammonium acetate can be commercially available, or can be prepared by the use of known techniques.

Next, —COO—R$^1$ moiety of the compound (V) is converted to —CH$_2$—OH with the use of conventional ester reduction method using reducing agent such as lithium aluminum hydride, lithium borohydride, and sodium bis (2-methoxyethoxy) aluminum hydride (step1). Then the compound (VI) is converted to the compound (VII) by conventional circulization methods using e.g., phosgene, diphosgene and triphosgene (step2). The protecting groups in —OX and —NX' in the compound (VII) can be removed by the conventional methods, e.g., acid treatment to give the compound (VIII)(step3). The chiral isomer separation of compound (VIII) gave the compound (I). This chiral isomer separation is effected by, for example, liquid chromatografy using a chiral column consisting of optically active amino acid, sugar or others, preferably with HPLC or recrystalization method using optically active organic acid such as (-)-di-p-toluoyl-L-tertaric acid.

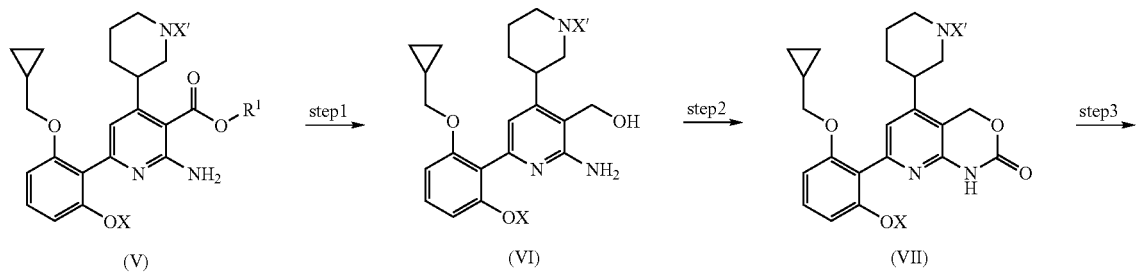

-continued

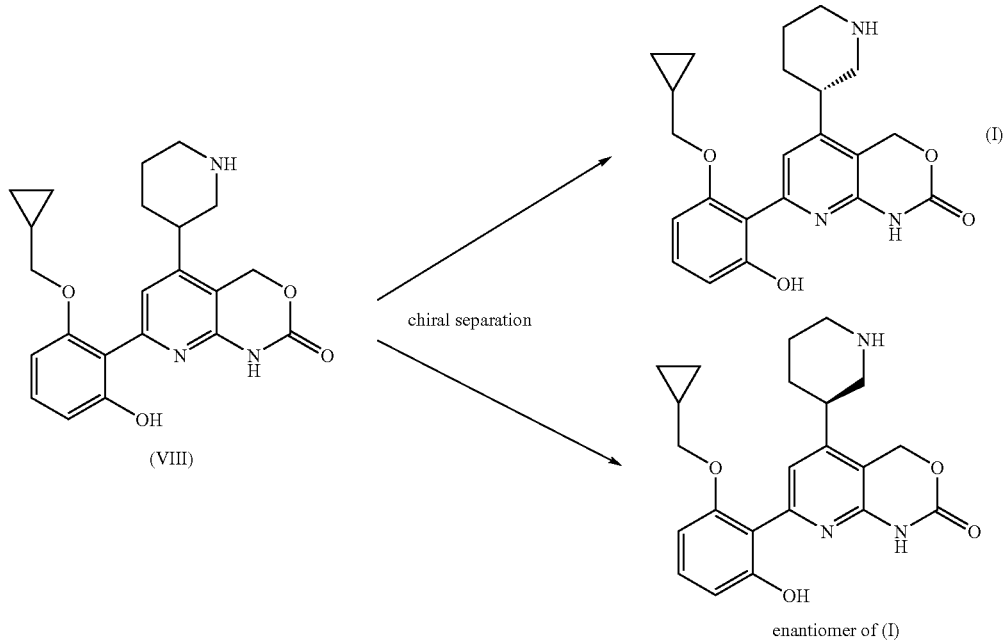

(VIII)

chiral separation (I)

enantiomer of (I)

The compound (I) can also be obtained when chiral separation step is performed before any of step1, step2 or step3.

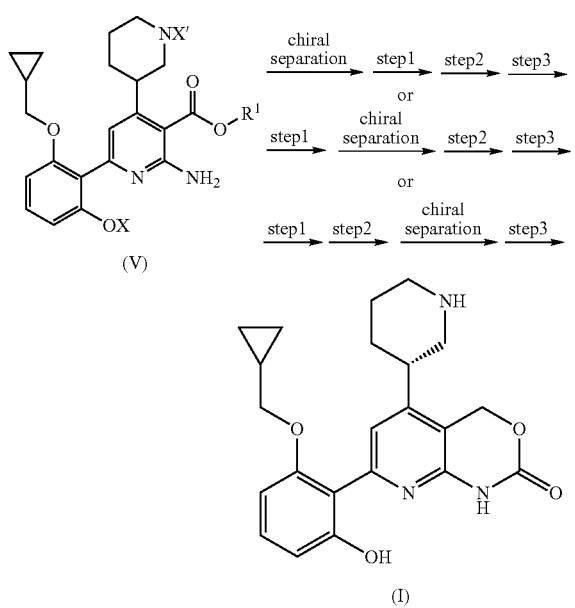

(V)

(I)

Typical salts of the compound shown by the formula (I) include salts prepared by reaction of the compound of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-tolu- enesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or a salts thereof, may be modified to form lower alkylesters or known other esters; and/or hydrates or other solvates. Those esters, hydrates, and solvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well known to those of ordinary skill in the pharmaceutical arts. The compounds of the present invention can be administered in intranasal form via topical use of suitable intranasal vehicles, or via transdermal routes, using transdermal delivery systems well known to those of ordinary skilled in the art.

The dosage regimen with the use of the compound of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compound of the present invention is preferably formulated prior to administration together with one or more pharmaceutically acceptable excipients. Excipients are inert substances such as, without limitation carriers, diluents, flavoring agents, sweeteners, lubricants, solubilizers, suspending agents, binders, tablet disintegrating agents and encapsulating material.

Yet, another embodiment of the present invention is pharmaceutical formulation comprising the compound of the invention and one or more pharmaceutically acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically acceptable excipients therefor. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, acacia, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid, which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

The effect of the present compound was examined by the following assays and pharmacological tests.

[IKK-β Kinase Inhibitory Assay]

(1) Preparation of IKK-β Kinase Protein

A cDNA fragment encoding human IKK-β open reading frame was generated by PCR with the use of a pair of primers designed from the published sequence (Woronicz J D et al. (1997) Science 278, 866-869). A template was obtained from Quickclone cDNA (Clontech) using Elongase™ Amplification kit (Life Technologies). The DNA fragments generated by PCR were gel-purified and subcloned into pBluescript. The cDNA fragment cloned in pBluescript was inserted into pcDNA3.1/His C KpnI/NotI, and transferred into pVL1393 SmaI/XbaI (Pharmingen) to construct a baculovirus transfer vector. Then the vector, together with the linearized baculovirus (BaculoGold™, Pharmingen) was used to transfect Sf21 cells (Invitrogen, San Diego, Calif.). Generated recombinant baculovirus was cloned and amplified in Sf21 cells, grown in TNM-FH insect cell medium (Life Technologies, Inc.) supplemented with 10% FCS, 50 g/ml Gentamycin, 0.1% Pluronic F68 (Life Technologies, Inc.) as suspension culture (200 ml in 1 L Erlenmeyer flask; 27° C.; 130 rpm). Sf21 cells were infected with this amplified virus with a multiplicity of infection of 5 following standard protocols (Crossen R, Gruenwald S (1997) Baculovirus Expression Vector System Instruction Manual, Pharmingen Corporation) and harvested 48 hrs later. The cells were lysed to obtain the produced chimeric protein of IKK-β kinase fused by histidine (His-tagged IKK-beta).

(2) The Preparation of Purified GST-IκBα Fusion Proteins

An expression vector containing the nucleotide sequence encoding fusion protein of GST with amino acid residues 1 to 54 of IκBα under the control of an IPTG-inducible promoter was constructed. The expression vector was introduced in *E. coli* and the transformant was cultured and lysed to obtain a GST-IκBα fusion protein. Then the resulting GST-IκBα fusion protein was purified and biotinated for kinase assay.

(3) The Measurement of IKK-β Kinase Activity

The 96-well format kinase assay of IKK-β were performed to test the inhibitory activity of the compounds of the present invention. First, 5 μl of a test compound was put in the presence of 2.5% dimethyl sulfoxide (DMSO) in each well in a U-bottomed 96-well plate (Falcon). For control wells of background (BG) and total phosphorylation (TP), 5 μl of 2.5% DMSO was put. Recombinant IKK-β (final 0.6 μg/ml) and bio-GST-IκBα (1-54) (final 0.2 μM) were diluted in 25 μl of 2× kinase buffer 0 (40 mM Tris-HCl, pH 7.6, 40 mM $MgCl_2$, 40 mM O-glycerophosphate, 40 mM p-nitrophenylphosphate, 2 mM EDTA, 40 mM creatine phosphate, 2 mM DTT, 2 mM $Na_3VO_4$, 0.2 mg/ml BSA and 0.8 mM phenylmethylsulfonyl fluoride) and transferred to the 96-well plate. Bio-GST-IκBα (1-54) in 25 μl of 2× kinase buffer β without IKK-β was transferred to BG wells. Then 20 μl of 12.5 μM ATP, 62.5 μCi/ml [$\gamma$-$^{33}$P] ATP (Amersham Pharmacia Biotech) was added and the resulting mixture was incubated for 2 hrs at room temperature. The kinase reactions were terminated by the addition of 150 μl of termination buffer (100 mM EDTA, 1 mg/ml BSA, 0.2 mg $NaN_3$). One hundred and fifty μl of the sample were transferred to a streptavidin-coated, white MTP (Steffens Biotechniche Analysen GmbH #08114E14.FWD) to capture the biotinylated substrates. After 1 hr of incubation, non-bound radioactivity was eliminated by washing the wells five times with 300 μl of washing buffer including 0.9% NaCl and 0.1% (w/v) Tween-20 with the use of a MW-96 plate washer (BioTec). The bound radioactivity was determined after the addition of 170 μl MicroScint-PS scintillation cocktail (Packard) using a TopCount scintillation counter.

[Syk Tyrosine Kinase Inhibitory Assay for Selectivity]

(1) Preparation of Syk Protein

A cDNA fragment encoding human Syk openreading frame was cloned from total RNA of human Burkitt's lymphoma B cell lines, Raji (American Type Culture Collection), with the use of RT-PCR method. The cDNA fragment was inserted into pAcG2T (Pharmingen, San Diego, Calif.) to construct a baculovirus transfer vector. Then the vector, together with the linearized baculovirus (BaculoGold™, Pharmingen), was used to transfect Sf21 cells (Invitrogen, San Diego, Calif.).

Generated recombinant baculovirus was cloned and amplified in Sf21 cells. Sf21 cells were infected with this amplified high titer virus to produce a chimeric protein of Syk kinase fused by glutathione-S-transferase (GST).

The resulting GST-Syk was purified with the use of glutathione column (Amersham Pharmacia Biotech AB, Uppsala, Sweden) according to the manufacturer's instruction. The purity of the protein was confirmed to be more than 90% by SDS-PAGE.

(2) Synthesize of a Peptide

Next, a peptide fragment of 30 residues including two tyrosine residues, KISDFGLSKALRADE-NYYKAQTHGKWPVKW, was synthesized by a peptide synthesizer. The N-terminal of the fragment was then biotinylated to obtain biotinylated activation loop peptide (AL).

(3) The Measurement of Syk Tyrosine Kinase Activity

All reagents were diluted with the Syk kinase assay buffer (50 mM Tris-HCl (pH 8.0), 10 mM $MgCl_2$, 0.1 mM $Na_3VO_4$, 0.1% BSA, 1 mM DTT). First, a mixture (35 μl) including 3.2 μg of GST-Syk and 0.5 μg of AL was put in each well in 96-well plates. Then 5 μd of a test compound in the presence of 2.5% dimethyl sulfoxide (DMSO) was added to each well. To this mixture was added 300 μM ATP (10 μl) to initiate the kinase reaction. The final reaction mixture (50 μl) consists of 0.65 nM GST-Syk, 3 μM AL, 30 μM ATP, a test compound, 0.25% DMSO, and a Syk kinase assay buffer.

The mixture was incubated for 1 hr at room temperature (RT), and the reaction was terminated by the addition of 120 μl of termination buffer (50 mM Tris-HCl (pH 8.0), 10 mM EDTA, 500 mM NaCl, 0.1% BSA). The mixture was transferred to streptavidin-coated plates and incubated for 30 min. at room temperature to combine biotin-AL to the plates. After washing the plates with Tris-buffered saline (TBS) (50 mM Tris-HCl (pH 8.0), 138 mM NaCl, 2.7 mM KCl) containing 0.05% Tween-20 for 3 times, 100 μl of antibody solution consisting of 50 mM Tris-HCl (pH 8.0), 138 mM NaCl, 2.7 mM KCl, 1% BSA, 60 ng/ml anti-phosphotyrosine monoclonal antibody, 4G10 (Upstate Biotechnology), which was labeled with europium by Amersham Pharmacia's kit in advance, was added and incubated at room temperature for 60 minutes. After washing, 100 μl of enhancement solution (Amersham Pharmacia Biotech) was added and then time-resolved fluorescence was measured by multi-label counter ARVO (Wallac Oy, Finland) at 340 nm for excitation and 615 nm for emission with 400 msec of delay and 400 msec of window.

[The Measurement of RANTES Production in Response to TNF-α from A549 cells]

(1) Preparation of A549 Cells

The A549 human lung epithelium cell line (ATCC #CCL-885) was maintained in Dulbecco's modified Eagle's medium (D-MEM, Nikken Biomedical Institute) supplemented with 10% FCS (Gibco), 100 U/ml penicillin, 100 μg/ml streptomycin, and 2 mM glutamine (culture medium). Forty thousand ($4\times10^4$) cells (80 μl/well) were seeded in each well of 96 well flat-bottom tissue culture plate (Falcon #3072). The plate was allowed to stand for 2 hrs, thus the cells were adhered to the bottom of each well. To the each well was added 10 μl vehicle (1% DMSO), serial dilutions of test compounds in 1% DMSO, or 5 nM Dexamethasone in 1% DMSO as a reference. The mixture (90 μl/well) was incubated for 1 hr at 37° C. After 1 hr, 1 μg/ml TNF-α (10 μl) in culture medium was added to the mixture to obtain 100 μl of reaction mixture. The reaction mixture was cultured for 24 hrs to stimulate the cells with 100 ng/ml TNF-α. Cells with vehicle without TNF-α stimulation were also prepared.

(2) Measurement of RANTES Production

Then the concentration of RANTES released from the cells in the supernatants of each well was determined using a quantitative sandwich enzyme immunoassay technique. First, 2 μg/ml mouse anti-huRANTES mAb (R&D Systems, #mAb678) in PBS buffer (pH 7.4, 1001 μl) was put in each well of 96-well NUNC fluoro plate (Nalge Nunc, New York USA) (Final 200 ng/well) and the plate was allowed to stand for overnight at 4° C. to be coated by the antibody. Each well of the plate was then washed with 350 µl wash buffer (0.05% Tween-20, 0.85% NaCl, and 25 mM Tris/HCl pH7.4) for three times. Blocking buffer containing 1% BSA (Sigma 99% pure, 100 g), 5% sucrose (Nacalai tesque, 99% pure, 500 g), and 0.02% azide (Nacalai tesque, 100%, 500 g) were added (200 µl) to each well and then the plate was allowed to stand for 4 hours to stabilize the coated antibody. Next, 50 µl supernatants of cell culture prepared in (1) above were put in each well of the 96-well NUNC fluoro plate with coated antibody. Recombinant Human RANTES (Pepro Tech, Inc. #300-06) was used as the standard for the determination of RANTES production (linear range between 1 and 10 ng/ml). Eu-labelled mouse anti-huRANES mAb (60 ng/ml: R&D Systems, #mAb278) in PBS supplemented by 1% BSA and 0.05% Tween 20 was added (50 µl) to each well. The reaction mixtures were incubated at room temperature for 4 hrs. After washing with wash buffer (0.05% Tween-20, 0.85% NaCl, and 25 mM Tris/HCl pH7.4, 350 µl/well) for 5 times with the use of a Sera Washer (Bio-Tech, #MW-96R), the enhancement solution (DELFIA, #1244-405, 100 µl/well) was added to each well. The plate was incubated for 10 minutes at room temperature with moderate shaking. Fluorescent intensity was measured using a DELFIA fluorimeter (Wallac). Excitation was performed at 340 nm and emission was measured at 615 nm.

[The Measurement of TNF-α Production in Response to LPS from Peripheral Blood Mononuclear Cells (PBMC)]

(1) Preparation of PBMC

Human PBMC were prepared by first obtaining blood from healthy donors and isolating the cells from the blood. The isolation was done by Ficoll gradient-centrifugation method using Ficoll Pacque (Pharmacia #17-1440-02). Within three hours from donation, the isolated PBMC was used. After three times washing with PBS, PBMC were resuspended with RPMI 1640 (Nikken BioMedical Institute) supplemented with 10% FCS (Gibco), 100 U/ml penicillin, 100 µg/ml streptomycin, and 2 mM glutamine (culture medium). The cells (1×10$^5$ in 150 µl/well) were seeded in each well of 96 well flat-bottom tissue culture plate (Falcon #3072). To the each well was added 20 µl vehicle (1% DMSO), serial dilutions of test compounds in 1% DMSO, or 250 nM Dexamethasone in 1% DMSO as a reference. The mixture (170 µl/well) was incubated for 1 hr at 37° C. After 1 hr, 20 ng/ml LPS (30 µl) in culture medium was added to the mixture to obtain 200 µl of reaction mixture. The reaction mixture was cultured for 7 hrs to stimulate the cells with 3 ng/ml LPS. Cells with vehicle without LPS stimulation were also prepared. The supernatants of the reaction mixture were then collected.

(2) Measurement of TNF-α Production

The TNF-α concentration in the supernatants was determined using a DuoSet™ ELISA Development Kit (GenzymeTechne, Minneapolis, USA) following the manufacturer's recommendations. First, 4 µg/ml of mouse anti-human TNF-α Ab in PBS buffer (100 µl) was put in each well of 96-well plate (NUNC, Maxisorp™) and the plate was allowed to stand for overnight at 4° C. to be coated with the antibody. Each well of the plate was then washed 5 times with 350 µl of wash buffer containing PBS, 0.05% Tween 20 (Nakalai tesque) using Sera Washer (Bio-Tech, #MW-96R). To each well was added 300 µl of 1% BSA (Sigma), 5% sucrose in PBS. After 2 hrs incubation at room temperature, the buffer was discarded, and 50 µl of culture medium was added. Next, 50 µl supernatant of stimulated cell culture prepared (1) above was put in each well of the 96-well plate. Recombinant human TNF-α (Genzyme Techne) was used as the standard for the determination of TNF-α production (linear range between 30 and 2,000 pg/ml). The reaction mixtures were incubated for 1 hr at room temperature. After 5 times washing, 100 µl biotinylated goat anti-human TNF-α antibody (Genzyme Techne, 300 ng/ml) in 0.1% BSA, 0.05% Tween in PBS (Reagent diluent) was added to each well, and incubated at room temperature for 1 hr. After 5 times washing, 100 µl of Streptavidin-conjugated horseradishperoxidase (Genzyme Techne, 1/100 in Reagent diluent) was added to each well. After 20 min, each well of the plate was washed 5 times with wash buffer (350 µl/well). The substrate of hourseradishperoxidase and $H_2O_2$ (TMBZ peroxidase detection kit, SUMILON #ML-1120T) were added to the mixture and the mixture was allowed to stand at room temperature. The reaction was terminated after 10 min by adding 2N $H_2SO_4$. Optical density at 450 nm was measured with the use of a microplate reader (Labosystems, Multiscan Multisoft). Quantification of TNF-α production in each sample was performed by comparison of optical densities between each sample and the standard curve.

[The Measurement of IL-2 Production in Jurkat T Cells in Response to Antibody Stimulation]

IL-2 production was measured in Jurkat T cells (E6-1 clone; ATCC # TIB-152) in response to stimulation with anti-CD3/anti-CD28 antibodies.

(1) Preparation of Immobilized Antibodies

First, anti-CD3 antibodies (400 ng/well Nichirei, NU-T3 4 µg/ml in 100 µl Dulbecco's PBS) were put in each well of 96-well plate (Falcon #3072) and the plate was allowed to stand for 2 hrs at room temperature to be coated with the antibody. Each well of the plate was then washed with 250 µl PBS 3 times.

(2) Preparation of Jurkat Cell Culture

Jurkat T cells were cultured in RPMI 1640 medium supplemented with 10% heat-inactivated fetal calf serum, 2 mM L-glutamine, 100 U/ml penicillin G, and 100 µg/ml streptomycin (culture medium). Two hundred thousand (2×10$^5$) cells (190 µl/well) were seeded in each well of 96-well U-bottom tissue culture plates (Falcon #3077). To each well was added 10 µl vehicle (0.2% DMSO), serial dilution of compounds in 0.2% DMSO, or 25 nM cyclosporin A as a reference in 0.2% DMSO. The mixture (200 µl) was incubated for one hour at 37° C. in a humidified 5% $CO_2$ environment.

(3) Stimulation of the Cell

The reaction mixture obtained in (2) (100 µl) was put in the each well of the antibody-immobilized plate prepared in (1). To this well was added anti-CD28 antibodies (Nichirei, KOLT-2, 6 µg/ml in cell culture medium, 50 µl/well) and 2.5 µg/ml goat anti-mouse kappa chain antibodies (Bethyl Laboratories, (Cat#A90-119A) 10 µg/ml in culture medium, 50 µl/well). The reaction mixture in each well was incubated for 24 hrs at 37° C. to stimulate cells with immobilized anti-CD3 antibodies (400 ng/well) and anti-CD28 antibodies (1.5 μg/ml), and then to cross-link receptors on the cells with anti-mouse kappa chain antibodies (2.5 μg/ml).

(4) Measurement of IL-2 Production

The supernatants of the reaction mixture were then collected. The IL-2 concentration in the supernatants was determined using a DuoSet™ ELISA Development Kit (GenzymeTechne, Minneapolis, USA) following the manufacturer's recommendations. First, 2 μg/ml of mouse anti-huIL-2 Ab in PBS buffer (100 μl) was put in each well of 96-well plate (NUNC, Maxisorp™) and the plate was allowed to stand for overnight at 4° C. to be coated with the antibody. Each well of the plate was then washed 5 times with 350 μl of wash buffer containing PBS, 0.05% Tween 20 (Nakalai tesque) using Sera Washer (Bio-Tech, #MW-96R). To each well was added 250 μl of 1% BSA (Sigma) in PBS, 0.05% Tween 20 (dilution buffer). After 2 hrs incubation at room temperature, the buffer was discarded, and 50 μl of culture medium was added. Next, 50 μl supernatant of stimulated cell culture prepared (3) above was put in each well of the 96-well plate with coated mouse anti-huIL-2 antibody. Recombinant Human IL-2 (Genzyme Techne) was used as the standard for the determination of IL-2 production (linear range between 200 and 5,400 pg/ml). The reaction mixtures were incubated for 1 hr at room temperature. After 5 times washing, 100 μl biotinylated rabbit anti-huIL-2 antibody (Genzyme Techne, 1.25 μg/ml) in dilution buffer was added to each well, and incubated at room temperature for 1 hr. After 5 times washing, 100 μl of Streptavidin-conjugated horseradishperoxidase (Genzyme Techne, 1/1000 in dilution buffer) was added to each well. After 20 min, each well of the plate was washed 5 times with wash buffer (350 μl/well). Substrate and $H_2O_2$ (TMBZ peroxidase detection kit, SUMILON #ML-1120T) were added to the mixture and the mixture was allowed to stand at room temperature. The reaction was terminated after 10 min by adding 2N $H_2SO_4$. Optical density at 450 nm was measured with the use of a microplate reader (Labosystems, Multiscan Multisoft). Quantification of IL-2 production in each sample was performed by comparison of optical densities between each sample and the standard curve.

[Mouse LPS-Induced TNF-α Production]

Eight weeks old BALB/c female mice were placed into two groups, a control group and a treated group. A solution containing 200 μg/mouse of LPS in 0.9% physiological salt was administered by intraperitoneal (ip) injection into the control mice. Mice in the treated group were first injected ip with compounds of the present invention 30 minutes prior to the LPS injection. Under anesthesia with pentobarbital (80 mg/kg, i.p.), blood was collected from the posterior venous cavity of the treated and control mice at 90 min post-LPS injection into 96-well plate containing 2% EDTA solution. The plasma was separated by centrifugation at 1800 rpm for 10 minutes at 4° C. and then diluted with four times volumes of phosphate buffer saline (pH 7.4) containing 1% bovine serum albumin. TNF-α concentration in the sample was determined using an ELISA kit (Pharmingen, San Diego, Calif.)

The mean TNF-α level in 5 mice from each group was determined and the percent reduction in TNF-α levels was calculated. The treated mice showed significant decrease in the level of TNF-α as compared to the control mice. The result indicates that the compounds of the present invention can restrain LPS-induced cytokine activity.

[Rat LPS-Induced TNF-α Production]

Seven weeks old Wistar female rats were used. One mg of LPS (lypopolysaccharide) dissolved in phosphate buffer saline (pH 7.4) was administered intraperitoneally (i.p.) to rats. Compounds were given orally 60 minutes prior to the LPS injection. Under anesthesia with pentobarbital (80 mg/kg, i.p.), blood was collected from the posterior venous cavity of the rats 120 minutes post-LPS injection and added into 96-well plate containing 2% EDTA solution. The plasma was separated by centrifugation at 1800 rpm for 10 minutes at 4° C. and then diluted with four times volumes of phosphate buffer saline (H 7.4) containing 1% bovine serum albumin. TNF-α concentration in the sample was determined using an ELISA kit (Endogen, Boston, Mass.).

The mean TNF-α level in 7-8 rats from each group was determined and the percent reduction in TNF-α levels was calculated. The treated rats, given the compounds, showed significant decrease in the level of TNF-α as compared to the control rats. The result indicates that the compounds of the present invention can restrain LPS-induced cytokine activity.

Results of in vitro test are shown in Examples below. The data corresponds to the compounds as yielded by solid phase synthesis and thus to levels of purity of about 40 to 90%. The compound of the present invention also shows excellent selectivity and strong activity in cellular assays and in vivo assays. More concretely, the compound of the present invention shows cellular activity twice as strong as corresponding racemic modification. Also, the compound of the present invention shows anti-inflammatory activity twice as strong as corresponding racemic modification in Rat. Further, the compound was confirmed to be non-mutagenic according to the Ames-Test Screening.

EXAMPLES

The present invention will be described in detail below in the form of examples, but they should by no means be construed as defining the metes and bounds of the present invention. In the examples below, all quantitative data, if not stated otherwise, relate to percentages by weight. Mass spectra were obtained using electrospray (ES) ionization techniques (micromass Platform LC). Melting points are uncorrected. Liquid Chromatography-Mass spectroscopy (LC-MS) data were recorded on a Micromass Platform LC with Shimadzu Phenomenex ODS column (4.6 mm×30 mm) flushing a mixture of acetonitrile-water (9:1 to 1:9) at 1 ml/min of the flow rate. TLC was performed on a precoated silica gel plate (Merck silica gel 60 F-254). Silica gel (WAKO-gel C-200 (75-150 elm)) was used for all column chromatography separations. All chemicals were reagent grade and were purchased from Sigma-Aldrich, Wako pure chemical industries, Ltd., Tokyo kasei kogyo co. Ltd.

Proton nuclear magnetic resonance (1H NMR) spectra were recorded at either 300 or 500 MHz by Bruker DRX-300. 500 Bruker UltraShield™ and chemical shifts are reported in parts per million relative to tetramethylsilane (TMS).

Example 1

1-{2-[(cyclopropylmethyl)oxy]-hydroxyphenyl}ethanone

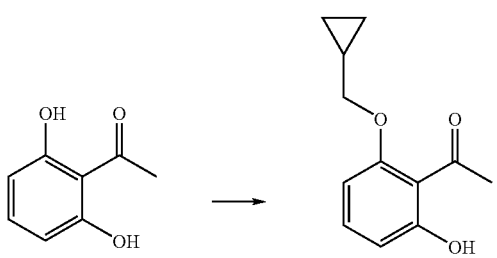

To a stirred solution of 1-(2,6-dihydroxyphenyl)ethanone (50.0 g, 328 mmol) in acetone (1000 mL) were added potassium carbonate (227 g, 1643 mmol) and (bromomethyl)cyclopropane (35.1 mL, 361 mmol). The mixture was stirred at 50° C. for 2 days. The reaction mixture was filtrated on Celite®, and then the filtrate was concentrated under reduced pressure. The residue was diluted with water and extracted with ethyl acetate. The separated organic phase was washed with water and brine, dried over MgSO$_4$, filtered and concentrated under reduced pressure. The residue was suspended in hexane. Then the suspension was stirred at 80° C. for 30 min. The solution was filtered and the filtrate was allowed to cool to room temperature. The resulting white solid was collected by filtration, washed with hexane, and dried under reduced pressure to give 1-{2-[(cyclopropylmethyl)oxy]-6-hydroxyphenyl} ethanone as a pale yellow solid (56.3 g, yield; 83%).

1-{2-(cyclopropylmethoxy)-6-[(4-methoxybenzyl)oxy]phenyl}ethanone

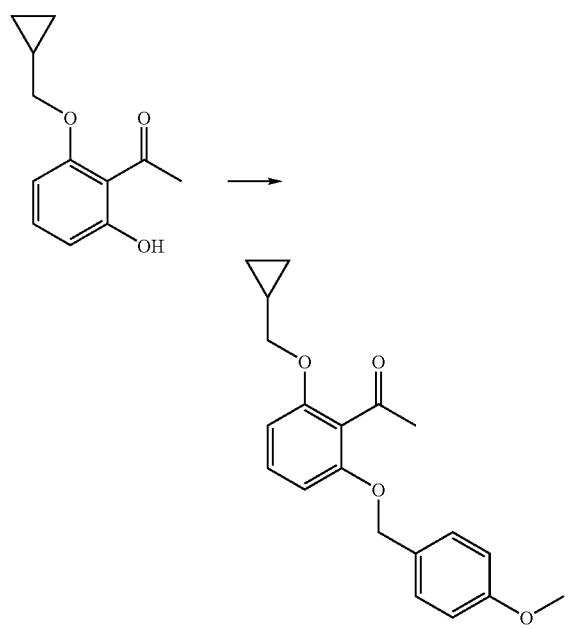

To a stirred solution of 1-{2-[(cyclopropylmethyl)oxy]-6-hydroxyphenyl}ethanone (56.3 g, 272 mmol) in acetone (1000 mL) were added potassium carbonate (188 g, 1364 mmol), 4-methoxybenzyl chloride (40.9 mL, 300 mmol) and tetrabutyl-ammonium iodide (20.2 g, 54.6 mmol). The mixture was stirred at reflux overnight. The reaction mixture was allowed to cool to room temperature, filtered on Celite®, and then the filtrate was concentrated under reduced pressure. The residue was diluted with water and extracted with ethyl acetate. The separated organic phase was washed with brine, dried over MgSO$_4$, filtered and concentrated under reduced pressure. Then the resulting white solid was recrystallized from ethanol, collected by filtration, washed with ethanol, and dried under reduced pressure to give 1-{2-(cyclopropylmethoxy)-6-[(4-methoxybenzyl)oxy]phenyl}ethanone as a white solid (79.2 g, yield; 89%).

tert-butyl 2-amino-4-[1-(tert-butoxycarbonyl)-3-piperidinyl]-6-{2-(cyclopropyl-methoxy)-6-[(4-methoxybenzyl)oxy]phenyl}nicotinate

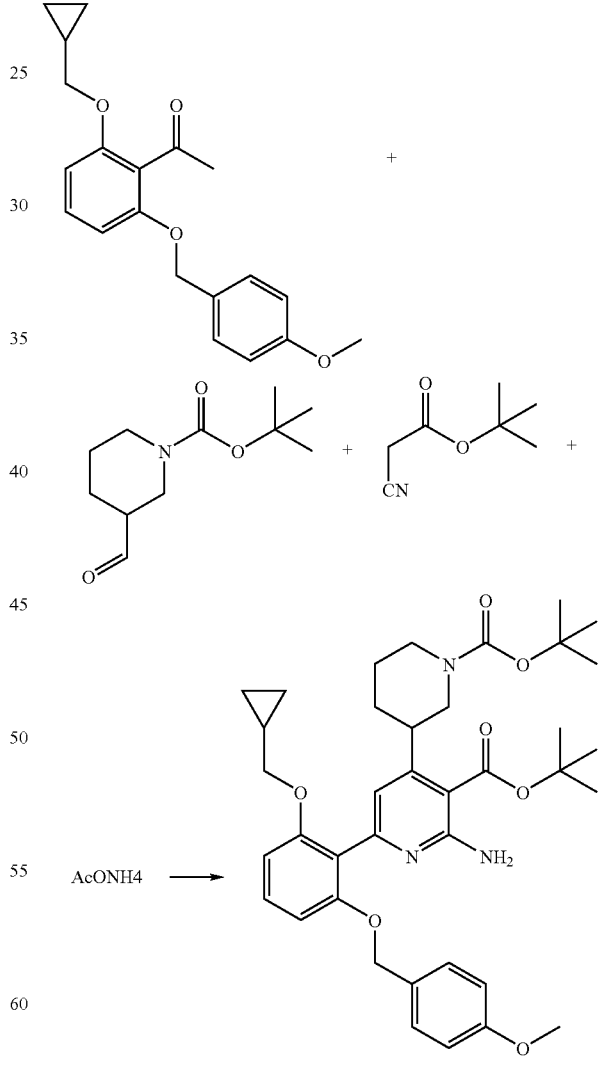

A mixture of 1-{2-(cyclopropylmethoxy)-6-[(4-methoxybenzyl)oxy]phenyl}ethanone (10.00 g, 30.638 mmol), tert-butyl 3-formyl-1-piperidinecarboxylate (13.069 g, 61.275 mmol), tert-butylcyanoacetate (8.650 g, 61.275 mmol), and ammonium acetate (6.902 g, 91.913 mmol) in dioxane (10 mL) was stirred at 90° C. overnight. After cooled to room temperature, the reaction mixture was diluted with ethyl acetate (100 mL). To the mixture was added chloranil (1.507 g, 6.128 mmol), and stirred at room temperature. After 1.5 hrs, ascorbic acid (1.079 g, 6.128 mmol) was added to the mixture. After stirred for 1.5 hrs, the mixture was partitioned between ethyl acetate and water. The organic phase was washed with brine, dried over MgSO$_4$, filtered, and then concentrated under reduced pressure. The resulting residue was purified by column chromatography on Silica-gel (hexane/ethyl acetate=2/1) to give tert-butyl 2-amino-4-[1-(tert-butoxycarbonyl)-3-piperidinyl]-6-{2-(cyclopropyl-methoxy)-6-[(4-methoxybenzyl)oxy]phenyl}nicotinate as a pale brown form (4.9 g, 24%).

tert-butyl 3-[2-amino-6-{2-(cyclopropylmethoxy)-6-[(4-methoxybenzyl)oxy]-phenyl}-3-(hydroxymethyl)-4-pyridinyl]-1-piperidinecarboxylate

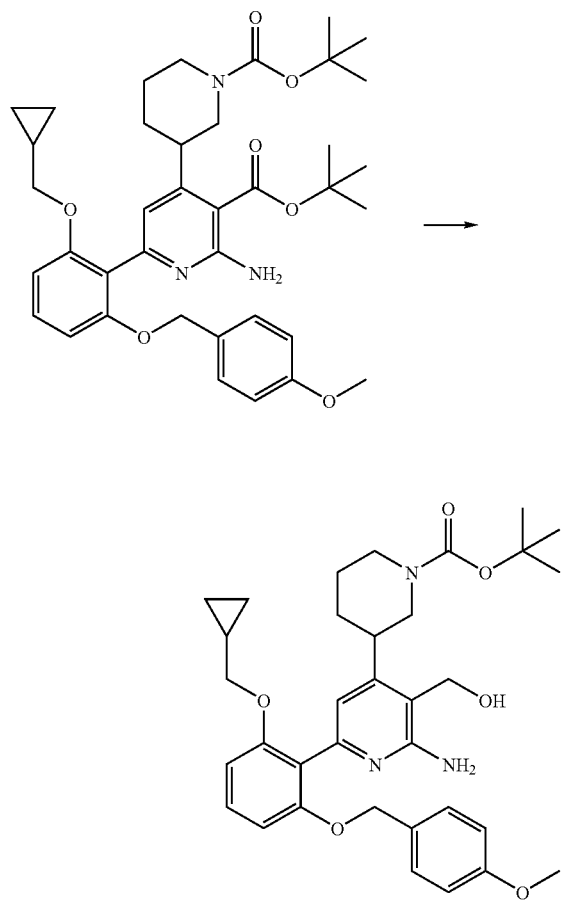

To a cooled solution of tert-butyl 2-amino-4-[1-(tert-butoxycarbonyl)-3-piperidinyl]-6-{2-(cyclopropylmethoxy)-6-[(4-methoxybenzyl)oxy]phenyl}nicotinate (4.9 g, 7.426 mmol) in tetrahydrofuran (60 mL) was added dropwise Vitride® (10 mL) under an argon atmosphere. The stirring was continued at 0° C. for 1 hr. After quenched by saturated aqueous NH$_4$Cl solution, saturated aqueous potassium sodium tartrate was added to the mixture, then the mixture was stirred vigorously. The mixture was extracted with ethyl acetate, washed with water and brine, dried over MgSO$_4$, filtered, and concentrated under reduced pressure to give tert-butyl 3-[2-amino-6-{2-(cyclopropylmethoxy)-6-[(4-methoxybenzyl)oxy]phenyl}-3-(hydroxymethyl)-4-pyridinyl]-1-piperidinecarboxylate, which was used for the next step without further purification (4.38 g, yield; quant.).

tert-butyl 3-(7-{2-(cyclopropylmethoxy)-6-[(4-methoxybenzyl)oxy]phenyl}-2-oxo-1,4-dihydro-2H-pyrido[2,3-d][1,3]oxazin-5-yl)-1-piperidinecarboxylate

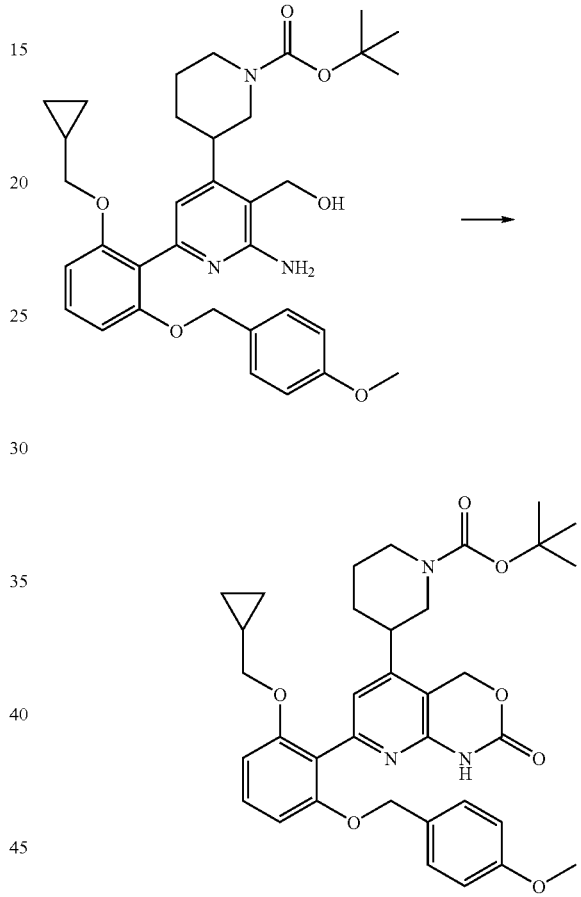

To a cooled (0° C.) solution of tert-butyl 3-[2-amino-6-{2-(cyclopropylmethoxy)-6-[(4-methoxybenzyl)oxy]phenyl}-3-(hydroxymethyl)-4-pyridinyl]-1-piperidine-carboxylate (5.0 g, 8.478 mmol), which was obtained in the step (2) of Example 17-1, and diisopropylethyl amine (4.12 mL, 25.435 mmol) in tetrahydrofuran (200 mL) under argon atmosphere was added dropwise to a solution of triphosgene (1.258 g, 4.239 mmol) in tetrahydrofuran (100 mL). The mixture was allowed to warm to room temperature, and the stirring was continued for 3 hrs. After quenched by water, the mixture was extracted with ethyl acetate. The separated organic phase was washed with brine, dried over MgSO$_4$, filtered, and concentrated under reduced pressure. The resulting residue was purified by column chromatography on Silica-gel (hexane/ethyl acetate=1/1) to give tert-butyl 3-(7-{2-(cyclopropylmethoxy)-6-[(4-methoxybenzyl)oxy]phenyl}-2-oxo-1,4-dihydro-2H-pyrido[2,3-d][1,3]oxazin-5-yl)-1-piperidinecarboxylate as a white form (3.2 g, yield; 61%).

7-[2-(cyclopropylmethoxy)-6-hydroxyphenyl]-5-(3-piperidinyl)-1,4-dihydro-2H-pyrido[2,3-d][1,3]oxazin-2-one hydrochloride

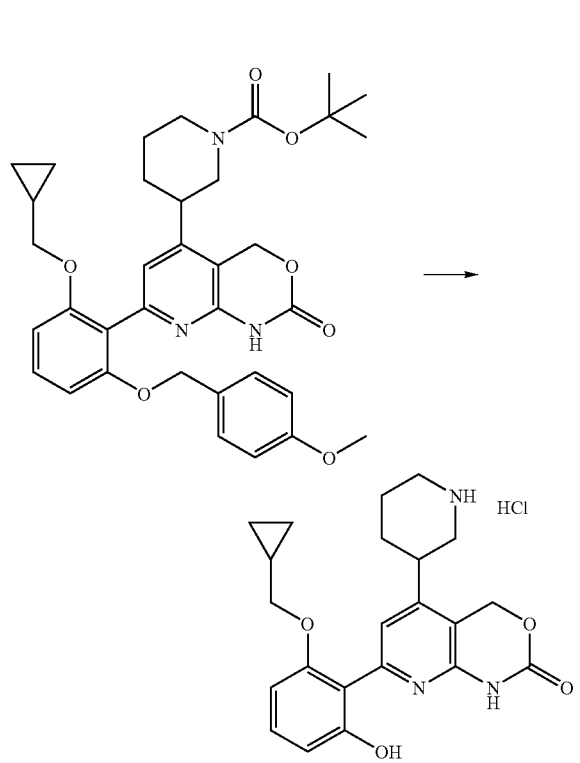

To a solution of tert-butyl 3-(7-{2-(cyclopropylmethoxy)-6-[(4-methoxybenzyl) oxy]phenyl}-2-oxo-1,4-dihydro-2H-pyrido[2,3-d][1,3]oxazin-5-yl)-1-piperidine-carboxylate (2.0 g, 3.248 mmol) in dioxane (15 mL) was added 4N HCl in dioxane (30 mL) at room temperature. The stirring was continued for 3 hrs. After the solvent was removed by evaporation, the resulting solid was triturated with acetonitrile, collected by filtration, and washed with acetonitrile. The solid was dried under reduced pressure to give 7-[2-(cyclopropylmethoxy)-6-hydroxyphenyl]-5-(3-piperidinyl)-1,4-dihydro-2H-pyrido[2,3-d][1,3]oxazin-2-one hydrochloride as a white solid (0.865 g, yield; 62%).

(−)-7-[2-cyclopropylmethoxy)-6-hydroxyphenyl]-5-[(3S)-3-pipeidinyl]-1,4-dihydro-2H-pyrido[2,3-d][1,3]oxazin-2-one (−)-di-p-toluoyl-L-tertaric acid salt

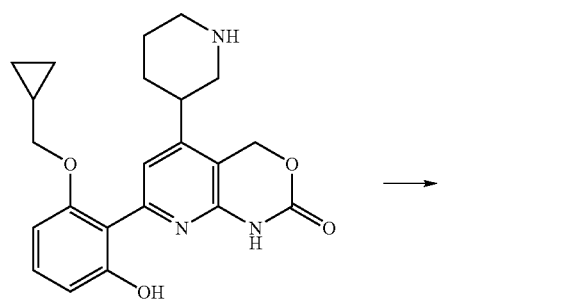

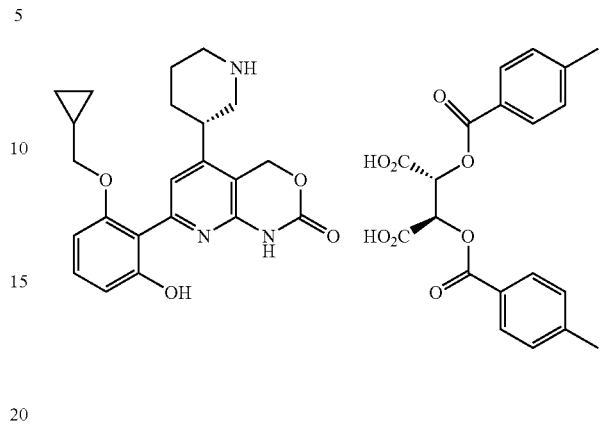

A mixture of 7-[2-(cyclopropylmethoxy)-6-hydroxyphenyl]-5-(3-piperidinyl) 1,4-dihydro-2H-pyrido[2,3-d][1,3]oxazin-2-one (0.700 g, 1.770 mmol) and (−)-di-p-toluoyl-L-tertaric acid (0.684 g, 0.213 mmol) was dissolved in a mixture of ethanol (30 mL) and water (3.0 mL) by heating. The mixture was allowed to cool to room temperature and stand overnight. The resulting precipitate was collected by filtration and washed with ethanol (85% ee). The product was again recrystallized from the same solvent (10% water/ethanol) and dried under reduced pressure to give (−)-7-[2-(cyclopropylmethoxy)-6-hydroxyphenyl]-5-[(3S)-3-piperidinyl]-1,4-dihydro-2H-pyrido[2,3-d][1,3]oxazin-2-one (−)-di-p-toluoyl-L-tertaric acid salt (0.115 g, >98% ee, yield; 8%).

Example 2 tert-butyl (3S)-(−)-3-(7-(2-(cyclopropylmethoxy)-6-((4-methoxybenzyl)oxy]phenyl)-2-oxo-1,4-dihydro-2H pyrido[2,3-d][1,3]oxazin-5-yl)-1-piperidinecarboxylate

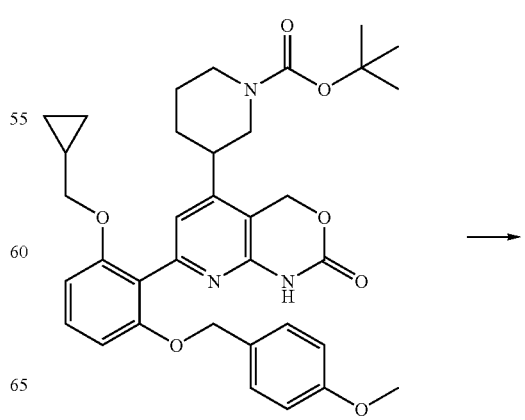

-continued

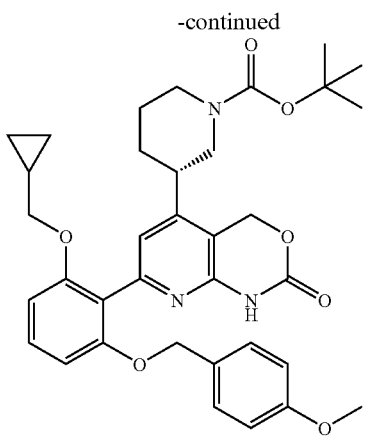

+

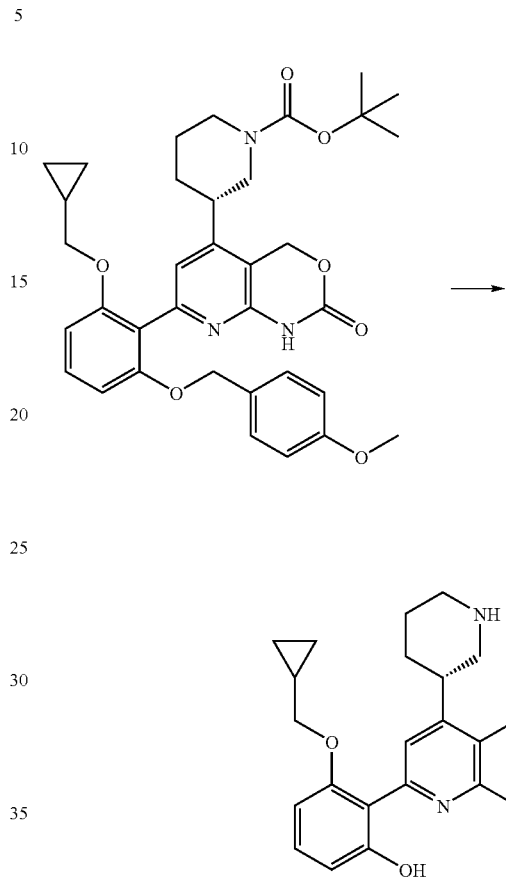

The chiral separation of tert-butyl 3-(7-({2-cyclopropylmethoxy)-6[(4-methoxybenzyl)oxy]phenyl}-2-oxo-1,4-dihydro-2H-pyrido[2,3-d][1,3]oxazin-5-yl)-1-piperidine-carboxylate was performed using HPLC under the following conditions:Column:Daisel CHIRALPAK OD (Daicel Chemical Industries, Ltd.)

Column size: 250*20 mm ID

Eluent: hexane/isopropanol, 60/40 (vol/vol)

Flow rate: 20 ml/min

Retention time: 31 min [(+)-isomer], 45 min [(−)-isomer]

The separated (−)-isomer, tert-butyl (3S)-(−)-3-(7-{2-(cyclopropylmethoxy)-6-[(4-methoxybenzyl)oxy]phenyl}-2-oxo-1,4-dihydro-2H-pyrido[2,3-d][1,3]oxazin-5-yl)

1-piperidinecarboxylate, was obtained as a colorless form.

Molecular weight: 615.73

Mass spectrometry: 616

$[\alpha]_D = -23.8°$ (CHCl$_3$, c=1.035, 23° C.)

The separated (+)-isomer, tert-butyl (3R)-(+)-3-(7-{2-(cyclopropylmethoxy)-6-[(4-methoxybenzyl)oxy]phenyl}-2-oxo-1,4-dihydro-2H-pyrido[2,3-d][1,3]oxazin-5-yl)-1-piperidinecarboxylate, was obtained as a colorless form.

Molecular weight: 615.73

Mass spectrometry: 616

$[\alpha]_D = +22.50$ (CHCl$_3$, c=1.012, 22° C.)

(−)-7-[2-(cyclopropylmethoxy)-6-hydroxyphenyl]-5-[(3S)-3-piperidinyl]-1,4-dihydro-2H-pyrido[2,3-d][1,3]oxazin-2-one hydrochloride To a solution of tert-butyl (3S)-(−)-3-(7-{2-(cyclopropylmethoxy)-6-[(4-methoxy-benzyl)oxy]phenyl}-2-oxo-1,4-dihydro-2H-pyrido[2,3-d][1,3]oxazin-5-yl)-1-piperidinecarboxylate (1.0 g, 1.624 mmol) in dioxane (15 mL) was added 4N HCl in dioxane (30 mL) at room temperature. The stirring was continued for 3 hrs. After the solvent was removed by evaporation, the resulting solid was triturated with acetonitril, collected by filtration, and washed with acetonitrile. The solid was recrystallized from methanol to give (−)-7-[2-(cyclopropylmethoxy)-6-hydroxy-phenyl]-5-[(3S)-3-piperidinyl]-1,4-dihydro-2H-pyrido[2,3-d][1,3]oxazin-2-one hydrochloride as a white solid (0.502 g, yield; 71%). The absolute configuration for the chiral atom was determined with (S) by the X-ray analysis.

Molecular weight: 431.92

Mass spectrometry: 396

Melting point: 260° C.

$[\alpha]_D = -21.1$ (DMF, c=0.908, 23° C.)

$^1$H-NMR (500 MHz, DMSO-d6): 0.26-0.37 (2H, m), 0.51-0.63 (2H, m), 1.20-1.31 (1H, m), 1.72-1.95 (4H, m), 2.80-2.96 (2H, m), 3.17-3.37 (3H, m), 3.79-3.88 (2H, m), 5.48 (1H, d, J=14.2 Hz), 5.53 (1H, d, J=14.2 Hz), 6354 (2H, d, J=8.2 Hz), 7.17 (1H, t, J=8.2 Hz), 7.77 (1H, s), 8.91 (1H, br), 9.11 (1H, br), 10.96 (1H, s), 11.62 (1H, s).

IKK-beta kinase inhibitory activity: IC$_{50}$=4 nM (+)-7-[2-(cyclopropylmethoxy)-6-hydroxyphenyl]-5-[(3R)-3-piperidinyl]-1,4-dihydro-2H-pyrido[2,3-d][1,3]oxazin-2-one hydrochloride

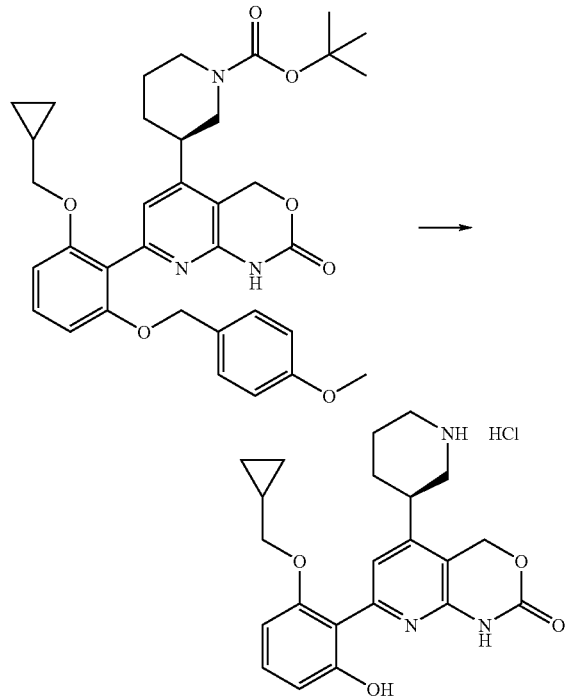

According to the similar synthetic procedure above, (+)-7-[2-(cyclopropylmethoxy)-6-hydroxyphenyl]-5-[(3R)-3-piperidinyl]-1,4-dihydro-2H-pyrido[2,3-d][1,3]oxazin-2-one hydrochloride was obtained as a white solid.

Molecular weight: 431.92
Mass spectrometry: 396
Melting point: 260° C.
$[\alpha]_D$=+21.5° (DMF, c=0.920, 25° C.)
IKK-beta kinase inhibitory activity: $IC_{50}$=59 nM

The invention claimed is:

1. An optically active (−)-7-[2-(cyclopropylmethoxy)-6-hydroxyphenyl]-5-[(3S)-3-piperidinyl]-1,4-dihydro-2H-pyrido[2,3-d][1,3]oxazin-2-one of the formula (I):

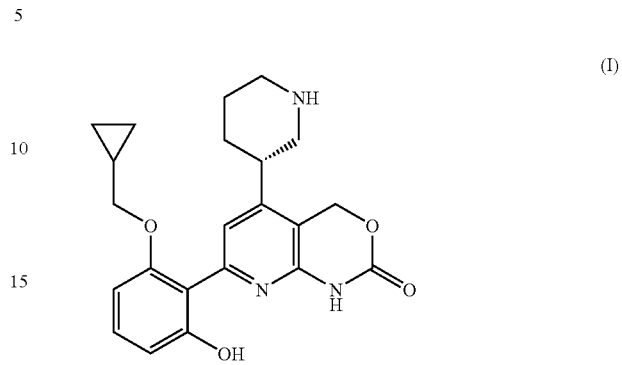

or a salt thereof.

2. The compound or a salt as claimed in claim 1, having an optical purity of at least 90% enantiomeric excess.

3. The compound or a salt as claimed in claim 1, having an optical purity of at least 95% enantiomeric excess.

4. A pharmaceutical composition comprising the compound or a salt thereof as claimed in claim 1, 2 or 3 and at least one pharmaceutically acceptable excipient.

5. A pharmaceutical composition having IκB kinase inhibitory activity comprising the compound or a salt thereof as claimed in claim 1 as an active ingredient, together with a pharmaceutically acceptable excipient.

6. A method of treating an inflammatory condition involving NF-κB activity selected from the group consisting of asthma; allergic rhinitis; atopic dermatitis; hives; conjunctivitis; vernal catarrh; chronic arthrorheumatism; systemic lupus erythematosus; psoriasis; diabrotic colitis; systemic inflammatory response syndrome (SIRS); polymyositis; dermatomyositis (DM); Polyaritis nodoa (PN); mixed connective tissue disease (MCTD); Sjoegren's syndrome; and gout in a subject, comprising administering to the subject an effective amount of the compound of claim 1, 2, or 3.

* * * * *